(12) United States Patent
Karino

(10) Patent No.: US 10,438,364 B2
(45) Date of Patent: Oct. 8, 2019

(54) SYSTEM AND METHOD FOR REGISTRATION OF PERFUSION IMAGES

(71) Applicant: FUJIFILM Corporation, Tokyo (JP)

(72) Inventor: Takatoshi Karino, Tokyo (JP)

(73) Assignee: FUJIFILM Corporation, Tokyo (JP)

(*) Notice: Subject to any disclaimer, the term of this patent is extended or adjusted under 35 U.S.C. 154(b) by 5 days.

(21) Appl. No.: 15/482,516

(22) Filed: Apr. 7, 2017

(65) Prior Publication Data

US 2017/0301083 A1    Oct. 19, 2017

(30) Foreign Application Priority Data

Apr. 13, 2016  (JP) .................................. 2016-079999

(51) Int. Cl.
*G06T 7/38* (2017.01)
*G06T 7/00* (2017.01)
(Continued)

(52) U.S. Cl.
CPC .......... *G06T 7/38* (2017.01); *A61B 2576/023* (2013.01); *G06T 7/0016* (2013.01); *G06T 7/30* (2017.01); *G06T 7/33* (2017.01); *G06T 2207/10081* (2013.01); *G06T 2207/20128* (2013.01); *G06T 2207/30048* (2013.01); *G06T 2207/30104* (2013.01)

(58) Field of Classification Search
CPC ................................ G06T 7/0016; G06T 7/30
USPC .......................................................... 382/128
See application file for complete search history.

(56) References Cited

U.S. PATENT DOCUMENTS

2012/0200741 A1\* 8/2012 Takahashi .......... H04N 5/23229
348/231.99
2012/0287131 A1  11/2012 Matsuzaki et al.
(Continued)

FOREIGN PATENT DOCUMENTS

JP    2011-125431 A    6/2011

OTHER PUBLICATIONS

Fieselmann et al., "Deconvolution-Based CT and MR Brain Perfusion Measurement: Theoretical Model Revisited and Practical Implementation Details", Hindawi Publishing Corporation, International Journal of Biomedical Imaging, vol. 2011, Article ID 467563, pp. 1-20.
(Continued)

*Primary Examiner* — Justin P. Misleh
(74) *Attorney, Agent, or Firm* — Birch, Stewart, Kolasch & Birch, LLP

(57) ABSTRACT

An image registration device includes: an image acquisition unit that acquires a plurality of images; a divided region setting unit that sets divided regions by dividing each registration processing target of the plurality of images; a pixel value conversion method determination unit that determines, for each set of divided regions set at the same position of the respective registration processing targets, a pixel value conversion method for each divided region based on a pixel value of each divided region of the set; a pixel value conversion unit that performs pixel value conversion within each divided region of the set of divided regions using the determined pixel value conversion method for each divided region; and a registration processing unit that performs registration processing on the plurality of images subjected to pixel value conversion.

26 Claims, 6 Drawing Sheets

(51) Int. Cl.
  *G06T 7/30*  (2017.01)
  *G06T 7/33*  (2017.01)

(56) References Cited

U.S. PATENT DOCUMENTS

| | | | |
|---|---|---|---|
| 2016/0022371 A1* | 1/2016 | Sauer | A61B 19/50 600/407 |
| 2016/0148375 A1* | 5/2016 | Oh | G06T 11/006 382/131 |
| 2016/0180526 A1* | 6/2016 | Satoh | G06T 5/007 382/131 |
| 2016/0232660 A1* | 8/2016 | Bannae | G06T 7/11 |

OTHER PUBLICATIONS

Mani et al., "Survey of Medical Image Registration", Journal of Biomedical Engineering and Technology, 2013, vol. 1, No. 2, pp. 8-25.

Miles, "Measurement of tissue perfusion by dynamic computed tomography", 1991, The British Journal of Radiology, vol. 64, No. 761, pp. 409-412.

* cited by examiner

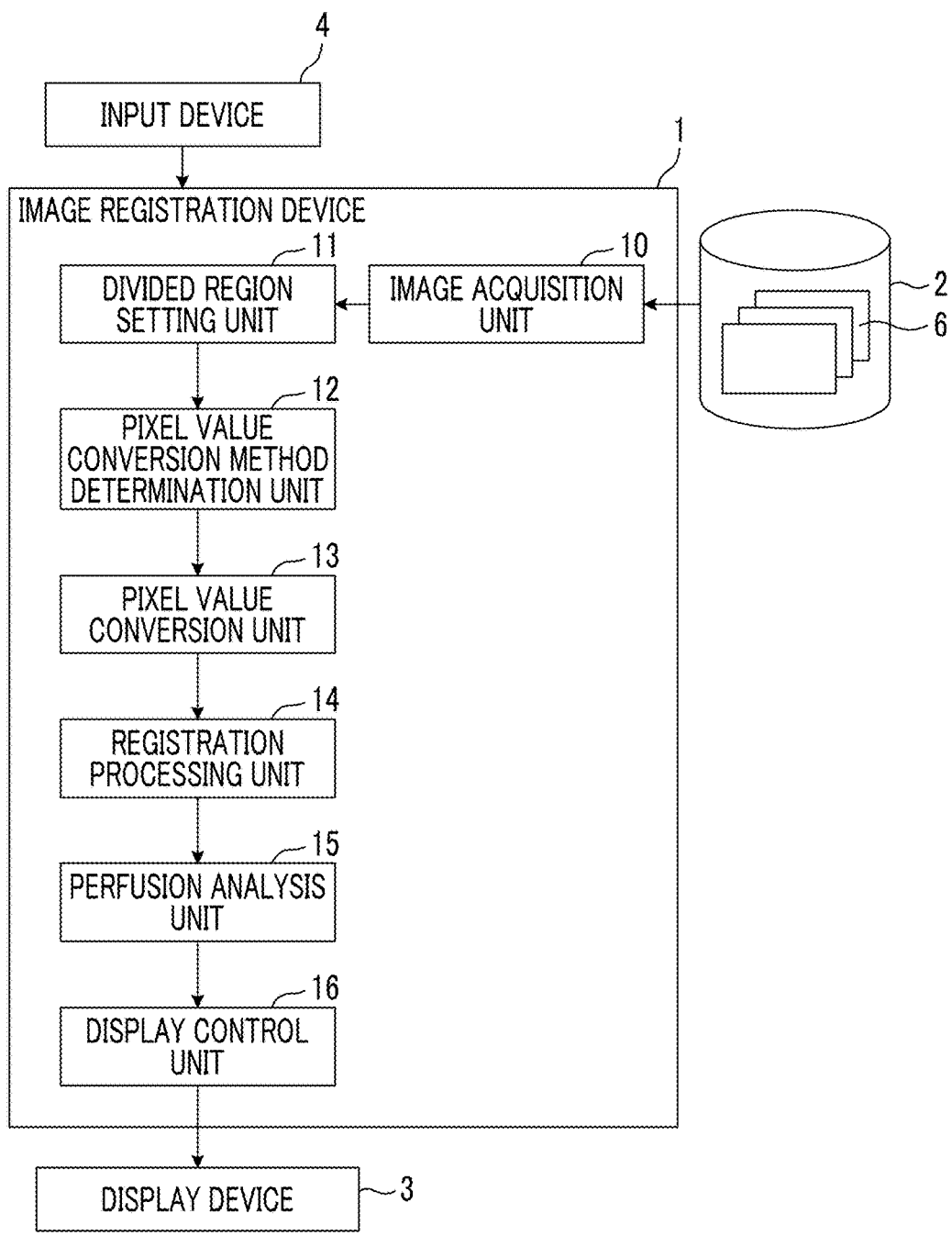

SYSTEM AND METHOD FOR REGISTRATION OF PERFUSION IMAGES

CROSS REFERENCE TO RELATED APPLICATIONS

The present application claims priority under 35 U.S.C. § 119 to Japanese Patent Application No. 2016-079999 filed on Apr. 13, 2016. The above application is hereby expressly incorporated by reference, in its entirety, into the present application.

BACKGROUND OF THE INVENTION

1. Field of the Invention

The present invention relates to an image registration device, method, and program for performing registration between a plurality of images.

2. Description of the Related Art

As a known method for measuring the blood flow rate in the myocardium, brain, liver, pancreas, and the like, perfusion imaging has been performed.

Perfusion imaging is an imaging method of injecting a contrast medium into a subject and imaging the subject a plurality of times at different timings using a computed tomography (CT) apparatus or the like. Depending on the phase (imaging timing), images with different anatomical structures contrasted are obtained. Specifically, in the case of the heart, the right atrium and the right ventricle are stained with a contrast medium by injecting the contrast medium through the vein in the initial phase. Then, the contrast medium flows in order of the left ventricle and the left atrium. As a result, the contrast of the cardiac image changes.

An image obtained by perfusion imaging is used for perfusion analysis. The main purpose of perfusion imaging and analysis is to analyze the blood flow of the target organ and diagnose the disease from the result. For example, the blood flow rate obtained by myocardial perfusion analysis is used for diagnosis of myocardial infarction.

As a quantitative analysis method of perfusion (blood flow), there is a maximum slope method (for example, refer to "Measurement of tissue perfusion by dynamic computed tomography.", Miles K A, The British journal of radiology (1991), Vol. 64, No. 761, pp. 409-412) or a deconvolution method (for example, refer to "Deconvolution-based CT and MR brain perfusion measurement: theoretical model revisited and practical implementation details", Fieselmann, Andreas and Kowarschik, Markus and Ganguly, Arundhuti and Hornegger, Joachim and Fahrig, Rebecca, Journal of Biomedical Imaging (2011), Vol. 2011, pp. 14). For these quantitative analyses, a "time density curve (hereinafter, referred to as TDC)" is used. The TDC represents a temporal change in pixel value (CT value) (temporal change in contrast medium concentration) at the position (region) of an organ.

In order to perform highly accurate quantitative analysis, it is necessary to accurately generate a TDC from an image obtained by perfusion imaging. For that purpose, it is necessary to generate a TDC from images of multiple phases by referring to pixel values of the same anatomical position (region). In this case, since it is necessary to accurately match the position of the target organ between phases, image registration is performed.

Registration between images is a problem of finding a geometric transformation T such that a point x of one image $I_F(x)$ (Fixed Image) and a point T(x) of the other image $I_M(x)$ (Moving Image) anatomically match each other. In a case where the geometric transformation T is described using a parameter μ, the registration between images is a problem of finding an optimal solution based on the following Equation (1). The geometric transformation T includes rigid transformation (translation and rotation), Affine transformation, non-rigid transformation (B-Spline and Diffeomorphism), and the like (for example, refer to "Survey of medical image registration", Mani, VRS and others, Journal of Biomedical Engineering and Technology (2013), Vol. 1, No. 2, pp. 8-25).

$$\hat{\mu} = \mathop{\mathrm{argmin}}_{\mu} S(I_F(\cdot), I_M(T(\cdot;\mu))) \tag{1}$$

S in the above Equation (1) is an evaluation function expressing the degree of matching between the image $I_F(x)$ and the image $I_M(T(\cdot; x))$. In this case, as S decreases, the degree of matching between the two images increases. As evaluation indices of the degree of matching, various evaluation indices, such as a sum of squared difference (SSD: sum of squares of pixel value differences at the same position between two images) or mutual information (one of indicators to quantify the statistical dependence between pixel values), are known.

SUMMARY OF THE INVENTION

Here, in the case of performing registration between images as described above, registration between images in which different anatomical structures are contrasted becomes a problem. For example, in a case where a structure having a high pixel value in one image shows a low pixel value in the other image, pixel values of the same region are different. Accordingly, since the degree of matching is evaluated to be low, it is not possible to perform accurate registration.

As a method of solving such a problem, a method of performing pixel value conversion on the entire image can be considered. Specifically, a method of converting a high pixel value to a low pixel value can be considered.

In the case of this method, however, information regarding the internal structure of an organ to be registered is lost. For example, in the case of myocardial perfusion images, there is a case where only the right atrium and the right ventricle show high pixel values due to the contrast medium in one of two images (refer to FIG. 2A) and not only the right atrium and the right ventricle but also the left atrium and the left ventricle show high pixel values in the other image (refer to FIG. 2B). In such a case, if the same pixel value conversion is applied to the entire image, the above problem can be solved with respect to the left atrium and the left ventricle for which only one image shows high pixel values, which is preferable. However, since both the right ventricle and the right atrium show high pixel values, shape information that can be used for registration is lost. For this reason, the position inside the organ cannot be adjusted.

JP2011-125431A discloses a technique relevant to registration between images captured by different modalities, such as a CT image and an ultrasound image, but a method of solving the problem described above has not been proposed.

In view of the aforementioned situation, it is an object of the invention to provide an image registration device, method, and program capable of performing registration with high accuracy by reducing the contrast difference between images even in a case where a structure having a high pixel value in one image shows a low pixel value in the other image.

A first image registration device of the invention comprises: an image acquisition unit that acquires a plurality of images including registration processing targets; a divided region setting unit that sets divided regions by dividing each of the registration processing targets of the plurality of images; a pixel value conversion method determination unit that determines, for each set of divided regions set at the same position of the respective registration processing targets, a pixel value conversion method for each divided region based on a pixel value of each divided region of the set; a pixel value conversion unit that performs pixel value conversion within each divided region of the set of divided regions using the pixel value conversion method for each divided region determined by the pixel value conversion method determination unit; and a registration processing unit that performs registration processing on the plurality of images subjected to pixel value conversion by the pixel value conversion unit.

In the first image registration device of the invention described above, the pixel value conversion method determination unit may determine whether or not to perform the pixel value conversion on each divided region based on the pixel value of each divided region of the set.

A second image registration device of the invention comprises: an image acquisition unit that acquires a plurality of images including registration processing targets; a divided region setting unit that sets divided regions by dividing each of the registration processing targets of the plurality of images; and a registration processing unit that performs registration processing by evaluating, for each set of divided regions set at the same position of the respective registration processing targets, a degree of matching between the respective divided regions of the set using an evaluation function, in which the registration processing unit changes, for each set of the divided regions, the evaluation function based on a pixel value of each divided region of the set, and performs the registration processing.

In the first and second image registration devices of the invention described above, the image acquisition unit may acquire an image including a cardiac image as the registration processing target, and the divided region setting unit may set, as the divided regions, a first divided region including a right atrium and a right ventricle and a second divided region including a left atrium and a left ventricle.

In the first and second image registration devices of the invention described above, the divided region setting unit may set the first and second divided regions based on a change in pixel value of a region of an aorta included in each of the plurality of images.

In the first and second image registration devices of the invention described above, the divided region setting unit may specify a first image, in which pixel values of regions of the right atrium and the right ventricle are higher than pixel values of regions of the left atrium and the left ventricle, and a second image, in which the pixel values of the regions of the left atrium and the left ventricle are higher than the pixel values of the regions of the right atrium and the right ventricle, among the plurality of images based on the change in pixel value of the region of the aorta included in each of the plurality of images, and set the first divided region using the first image and set the second divided region using the second image.

In the first and second image registration devices of the invention described above, the image acquisition unit may acquire an image including a cardiac image as the registration processing target, and the divided region setting unit may set, as the divided regions, a first divided region including a right atrium and a right ventricle, a second divided region including a left atrium and a left ventricle, and a third divided region including a myocardium.

In the first and second image registration devices of the invention described above, the image acquisition unit may acquire an image including a cardiac image as the registration processing target, and the divided region setting unit may set, as the divided regions, a first divided region including a right atrium, a second divided region including a right ventricle, a third divided region including a left atrium, and a fourth divided region including a left ventricle.

In the first and second image registration devices of the invention described above, the image acquisition unit may acquire an image including a cardiac image as the registration processing target, and the divided region setting unit may set, as the divided regions, a first divided region including a right atrium, a second divided region including a right ventricle, a third divided region including a left atrium, a fourth divided region including a left ventricle, and a fifth divided region including a myocardium.

In the first and second image registration devices of the invention described above, the image acquisition unit may acquire an image including a cardiac image as the registration processing target, and the divided region setting unit may set a plurality of divided regions by dividing the cardiac image with a cross section perpendicular to a blood flow direction of a heart.

In the first and second image registration devices of the invention described above, the divided region setting unit may set the divided regions for one of the plurality of images using a standard image in which regions corresponding to the divided regions are set in advance, and set divided regions for images other than the one image using a setting result of the divided regions.

In the first image registration device of the invention described above, the pixel value conversion unit may perform pixel value conversion for lowering a pixel value of an image within each of the divided regions.

In the first and second image registration devices of the invention described above, the image acquisition unit may acquire a plurality of images captured at different points in time.

In the first and second image registration devices of the invention described above, the image acquisition unit may acquire an image including a cardiac image as the registration processing target, and acquire a plurality of images captured at a timing of the same cardiac phase in a plurality of heart beats.

A first image registration method of the invention comprises: acquiring a plurality of images including registration processing targets; setting divided regions by dividing each of the registration processing targets of the plurality of images; determining, for each set of divided regions set at the same position of the respective registration processing targets, a pixel value conversion method for each divided region based on a pixel value of each divided region of the set; performing pixel value conversion within each divided region of the set of divided regions using the determined pixel value conversion method for each divided region; and performing registration processing on the plurality of images subjected to the pixel value conversion.

A second image registration method of the invention comprises: acquiring a plurality of images including registration processing targets; setting divided regions by dividing each of the registration processing targets of the plurality of images; and when performing registration processing by evaluating, for each set of divided regions set at the same position of the respective registration processing targets, a degree of matching between the respective divided regions of the set using an evaluation function, performing the registration processing by changing, for each set of the divided regions, the evaluation function based on a pixel value of each divided region of the set.

A first image registration program of the invention causes a computer to function as: an image acquisition unit that acquires a plurality of images including registration processing targets; a divided region setting unit that sets divided regions by dividing each of the registration processing targets of the plurality of images; a pixel value conversion method determination unit that determines, for each set of divided regions set at the same position of the respective registration processing targets, a pixel value conversion method for each divided region based on a pixel value of each divided region of the set; a pixel value conversion unit that performs pixel value conversion within each divided region of the set of divided regions using the pixel value conversion method for each divided region determined by the pixel value conversion method determination unit; and a registration processing unit that performs registration processing on the plurality of images subjected to pixel value conversion by the pixel value conversion unit.

A second image registration program of the invention causes a computer to function as: an image acquisition unit that acquires a plurality of images including registration processing targets; a divided region setting unit that sets divided regions by dividing each of the registration processing targets of the plurality of images; and a registration processing unit that performs registration processing by evaluating, for each set of divided regions set at the same position of the respective registration processing targets, a degree of matching between the respective divided regions of the set using an evaluation function. The registration processing unit changes, for each set of the divided regions, the evaluation function based on a pixel value of each divided region of the set, and performs the registration processing.

According to the first image registration device, method, and program of the invention, a plurality of images including registration processing targets are acquired, and divided regions are set by dividing each of the registration processing targets of the plurality of images. Then, for each set of divided regions set at the same position of the respective registration processing targets, a pixel value conversion method for each divided region is determined based on the pixel value of each divided region of the set. Pixel value conversion is performed on an image in each divided region of the set of divided regions using the determined pixel value conversion method for the divided region, and registration processing is performed on a plurality of images subjected to the pixel value conversion. By performing pixel value conversion using a pixel value conversion method that is determined for each divided region as described above, it is possible to reduce the contrast difference between images even in a case where a structure having a high pixel value in one image shows a low pixel value in the other image. As a result, it is possible to perform registration with high accuracy.

According to the second image registration device, method, and program of the invention, a plurality of images including registration processing targets are acquired, and divided regions are set by dividing each of the registration processing targets of the plurality of images. Then, for each set of divided regions set at the same position of the respective registration processing targets, registration processing is performed by evaluating the degree of matching between the respective divided regions of the set using an evaluation function. At this time, for each set of divided regions, by changing the evaluation function based on the pixel value of each divided region of the set, the registration processing is performed. By performing registration processing by changing the evaluation function for each divided region as described above, it is possible to reduce the contrast difference between images even in a case where a structure having a high pixel value in one image shows a low pixel value in the other image. As a result, it is possible to perform registration with high accuracy.

BRIEF DESCRIPTION OF THE DRAWINGS

FIG. 1 is a block diagram showing the schematic configuration of a medical image diagnosis assistance system using a first embodiment of an image registration device of the invention.

DESCRIPTION OF THE PREFERRED EMBODIMENTS

Figures 2A, 2B, 2C:
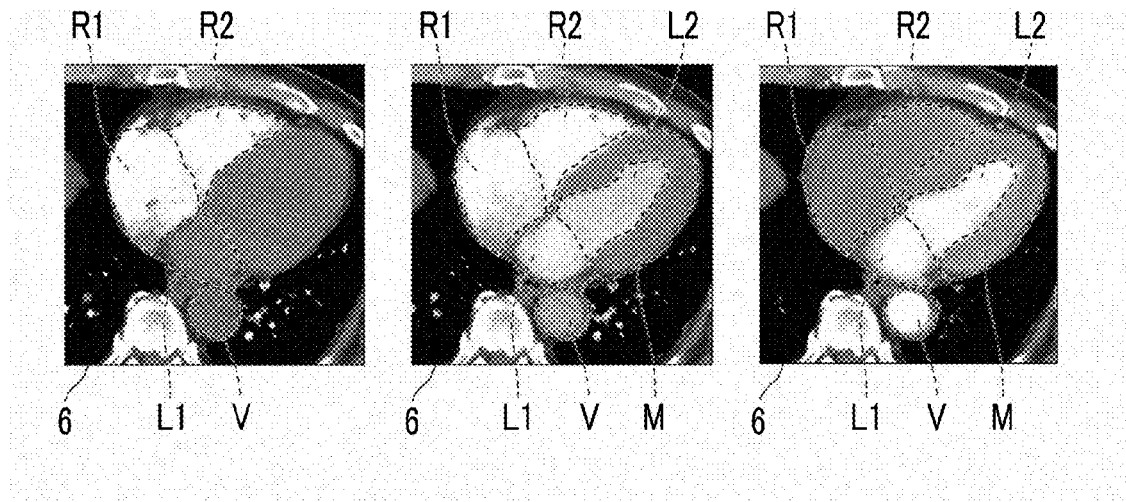
FIGS. 2A to 2C are diagrams showing examples of an image obtained by perfusion imaging of the heart.

Hereinafter, a medical image diagnosis assistance system using a first embodiment of an image registration device, method, and program of the invention will be described in detail with reference to the diagrams. FIG. 1 is a block diagram showing the schematic configuration of a medical image diagnosis assistance system of the present embodiment.

The medical image diagnosis assistance system of the present embodiment acquires two or more images by imaging the heart or the like at different points in time, performs registration between these images, and then performs perfusion analysis using the two or more images.

Specifically, as shown in FIG. 1, the medical image diagnosis assistance system of the present embodiment includes an image registration device 1, a medical image storage server 2, a display device 3, and an input device 4.

The image registration device 1 is formed by installing an image registration program of the present embodiment in a computer.

The image registration device 1 includes a central processing unit (CPU), a semiconductor memory, and a storage device such as a hard disk or a solid state drive (SSD). The image registration program of the present embodiment is installed in the storage device. When the image registration program is executed by the central processing unit, an image acquisition unit 10, a divided region setting unit 11, a pixel value conversion method determination unit 12, a pixel value conversion unit 13, a registration processing unit 14, a perfusion analysis unit 15, and a display control unit 16 that are shown in FIG. 1 operate.

The image registration program is distributed by being recorded on a recording medium, such as a digital versatile disc (DVD) and a compact disc read only memory (CD-ROM), and is installed into the computer from the recording medium. Alternatively, the image registration program is stored in a storage device of a server computer connected to the network or in a network storage so as to be accessible from the outside, and is downloaded and installed into the computer in response to a request.

The image acquisition unit 10 acquires a three-dimensional image 6 captured in advance. The three-dimensional image 6 is obtained by imaging a patient using a CT apparatus or a magnetic resonance imaging (MRI) apparatus, for example. The image acquisition unit 10 of the present embodiment acquires the three-dimensional image 6 captured by so-called perfusion imaging, and acquires cardiac images of two or more phases by imaging the heart, into which a contrast medium is injected, in time series.

More specifically, the image acquisition unit 10 acquires two or more cardiac images as the three-dimensional image 6 with one to several heart beats as an imaging interval. It is preferable that the two or more cardiac images are captured in the systole of each heart beat. There is no large difference in the shape of the heart contained in each cardiac image captured in the systole of each heart beat, but there is a deviation of about 1 cm. The deviation of about 1 cm is adjusted by registration processing, which will be described later. In the present embodiment, a systolic cardiac image is acquired. However, the invention is not limited thereto, and cardiac images of other phases may be acquired as long as these are cardiac images acquired at timings at which the shapes of the heart almost match each other.

In the present embodiment, the three-dimensional image 6 is acquired by imaging the heart into which a contrast medium is injected. However, the object to be imaged is not limited to the heart, and an image obtained by imaging the liver, the pancreas, the brain, or the like into which a contrast medium is injected may be acquired as the three-dimensional image 6.

As the three-dimensional image 6, volume data configured to include tomographic images, such as axial tomographic images, sagittal tomographic images, and coronal tomographic images, may be acquired, or a single tomographic image may be acquired.

The three-dimensional image 6 is stored in the medical image storage server 2 in advance together with the identification information of the patient, and the image acquisition unit 10 reads the three-dimensional image 6 having the identification information from the medical image storage server 2 based on the identification information of the patient, which has been input by the user using the input device 4 or the like, and temporarily stores the read three-dimensional image 6.

The divided region setting unit 11 sets divided regions by dividing each registration processing target included in two or more three-dimensional images 6 acquired by the image acquisition unit 10. The registration processing target in the present embodiment is the heart.

The divided region setting unit 11 of the present embodiment sets, as divided regions, a first divided region including the right atrium and the right ventricle and a second divided region including the left atrium and the left ventricle in a heart region in each three-dimensional image 6.

FIGS. 2A to 2C are diagrams showing examples of cardiac images captured in the systole of each heart beat. In FIGS. 2A to 2C, a region R1 is the region of the right atrium, a region R2 is the region of the right ventricle, a region L1 is the region of the left atrium, and a region L2 is the region of the left ventricle. In FIG. 2A, since the boundary between the left ventricle and the myocardium is not clear, the boundary between these regions is not shown. A region obtained by combining a region R1 and a region R2 is set as the first divided region, and a region obtained by combining a region L1 and a region L2 is set as the second divided region. A region M is a region of the myocardium, and a region V is a region of the aorta, and these regions will be described in detail later.

An atlas image (corresponding to the standard image of the invention) of the heart is preset in the divided region setting unit 11. In the atlas image, a standard three-dimensional image obtained by imaging the heart in advance is associated with a label image in which a region including the right atrium and the right ventricle and a region including the left atrium and the left ventricle are defined.

The divided region setting unit 11 sets first and second divided regions for the three-dimensional image 6 using the atlas image described above. Specifically, first, the divided region setting unit 11 performs registration processing between one representative three-dimensional image 6 of the two or more three-dimensional images 6 and the atlas image described above, thereby setting first and second divided regions for the representative three-dimensional image 6. As the registration processing, already known rigid registration processing or non-rigid registration processing can be used.

Then, first and second divided regions are set for the other three-dimensional images 6 using the setting result of the first and second divided regions of the representative three-dimensional image 6. Specifically, by associating the coordinate values of the first and second divided regions set in the representative three-dimensional image 6 with the other three-dimensional images 6, the first and second divided regions of the other three-dimensional images 6 are set. By applying the setting result of the divided regions of one representative three-dimensional image 6 to the other three-dimensional images 6 as described above, it is possible to reduce the load of divided region setting processing. As a result, it is possible to increase the processing speed.

Although the first and second divided regions of the other three-dimensional images 6 are set using the setting result of the first and second divided regions of the representative three-dimensional image 6 in the present embodiment, the invention is not limited thereto. For the other three-dimensional images 6 as well as the representative three-dimensional image 6, first and second divided regions may be set using the atlas image.

For each set of divided regions set at the same position of the heart included in each three-dimensional image 6, the pixel value conversion method determination unit 12 determines a pixel value conversion method for each divided region based on the pixel value of each divided region of the set. It is assumed that the pixel value conversion method in this specification includes "pixel value conversion is not performed".

Generally, since the pixel value of a contrasted portion in a cardiac image increases up to 100 or more, the pixel value conversion method determination unit 12 determines whether or not each divided region is contrasted using the numeric value, and determines a pixel value conversion method based on the determination result. For the sake of easy understanding, the following explanation will be focused on the relationship between two three-dimensional images 6 of the two or more three-dimensional images 6.

Specifically, the pixel value conversion method determination unit 12 calculates an average pixel value of the first divided region of the first three-dimensional image 6 and an average pixel value of the first divided region of the second three-dimensional image 6. Then, in a case where the average pixel value of the first divided region of the first three-dimensional image 6 is 100 or more and the average pixel value of the first divided region of the second three-dimensional image 6 is less than 100, that is, in a case where the contrast of the first divided region of the first three-dimensional image 6 is different from the contrast of the first divided region of the second three-dimensional image 6, it is determined to perform pixel value conversion for the pixel value of the first divided region of the first three-dimensional image 6.

Conversely, in a case where the average pixel value of the first divided region of the first three-dimensional image 6 is less than 100 and the average pixel value of the first divided region of the second three-dimensional image 6 is 100 or more, it is determined to perform pixel value conversion for the pixel value of the first divided region of the second three-dimensional image 6.

On the other hand, in a case where both the average pixel value of the first divided region of the first three-dimensional image 6 and the average pixel value of the first divided region of the second three-dimensional image 6 are 100 or more or less than 100, that is, in a case where both the contrast of the first divided region of the first three-dimensional image 6 and the contrast of the first divided region of the second three-dimensional image 6 are close to each other, it is determined that pixel value conversion is not performed for the first divided region of the first three-dimensional image 6 and the first divided region of the second three-dimensional image 6. In a case where both the average pixel value of the second divided region of the first three-dimensional image 6 and the average pixel value of the second divided region of the second three-dimensional image 6 are 100 or more or less than 100, it is determined that pixel value conversion is not performed for the second divided region of the first three-dimensional image 6 and the second divided region of the second three-dimensional image 6, in the same manner as for the first divided region.

Using the pixel value conversion method determined by the pixel value conversion method determination unit 12, the pixel value conversion unit 13 performs pixel value conversion for the first divided region of the first three-dimensional image 6 and the first divided region of the second three-dimensional image 6, and performs pixel value conversion for the second divided region of the first three-dimensional image 6 and the second divided region of the second three-dimensional image 6. Specifically, for an image in the divided region determined to perform pixel value conversion in the pixel value conversion method determination unit 12, the pixel value conversion is performed based on the following Equation (2). In the following Equation (2), x is a pixel value, and f(x) is a pixel value conversion function. By performing pixel value conversion based on the following Equation (2), it is possible to reduce a contrast difference between the first divided region of the first three-dimensional image 6 and the first divided region of the second three-dimensional image 6 or between the second divided region of the first three-dimensional image 6 and the second divided region of the second three-dimensional image 6.

$$f(x) = \begin{cases} x & (x < 50) \\ 50 + \log_e(x - 49) & (x \geq 50) \end{cases} \quad (2)$$

The registration processing unit 14 performs registration processing on the first three-dimensional image 6 and the second three-dimensional image 6 on which pixel value conversion has been performed by the pixel value conversion unit 13. As the registration processing, rigid registration processing or non-rigid registration processing is performed. As the rigid registration processing, for example, processing using an iterative closest point (ICP) method can be used. However, other known methods may be used. As the non-rigid registration processing, for example, processing using a free-form deformation (FFD) method or processing using a thin-plate spline (TPS) method can be used. However, other known methods may be used. In addition, after performing the rigid registration processing, the non-rigid registration processing may be performed.

Although the registration processing between two three-dimensional images of the first three-dimensional image 6 and the second three-dimensional image 6 has been described above, setting of a divided region, determination of a pixel value conversion method, pixel value conversion, and registration processing are performed in practice for a number (for example, 30 or more) of three-dimensional images 6 required for perfusion analysis.

Figures 3A, 3B:
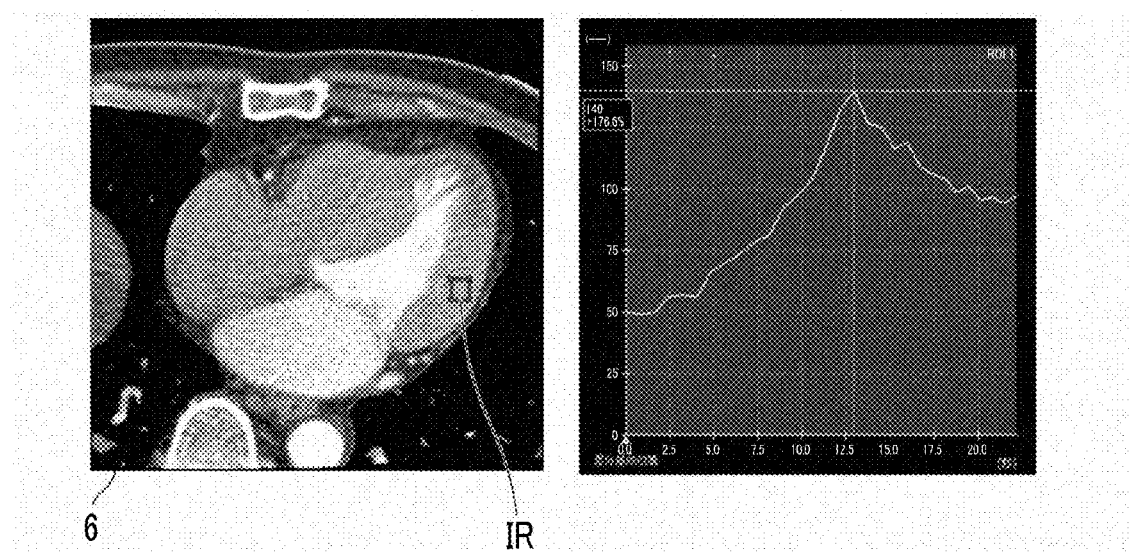
FIGS. 3A and 3B are diagrams illustrating an example of perfusion analysis.

The perfusion analysis unit 15 performs perfusion analysis using the two or more three-dimensional images 6 that have been subjected to registration processing by the registration processing unit 14. As a method of perfusion analysis, the maximum slope method or the deconvolution method described above is used. Specifically, as shown in FIG. 3A, a region of interest IR is designated on the three-dimensional image 6 displayed on the display device 3 by the user. The perfusion analysis unit 15 calculates an average density value in the region of interest IR of each of the two or more three-dimensional images 6 subjected to the registration processing, calculates a time density curve as shown in FIG. 3B, and performs perfusion analysis based on the time density curve.

The display control unit 16 includes a display device, such as a liquid crystal display, and displays the analysis result of the perfusion analysis unit 15 on the display device 3. In addition, the display control unit 16 displays the two or more three-dimensional images 6 acquired by the image acquisition unit 10, the two or more three-dimensional images 6 after registration processing, and the like on the display device 3.

The input device 4 receives various setting inputs from the user, and includes an input device, such as a keyboard or a mouse. For example, the input device 4 receives a setting input of the identification information of a patient, a setting input of the region of interest IR described above, and the like.

The display device 3 may also be used as the input device 4 by using a touch panel.

Figure 4:
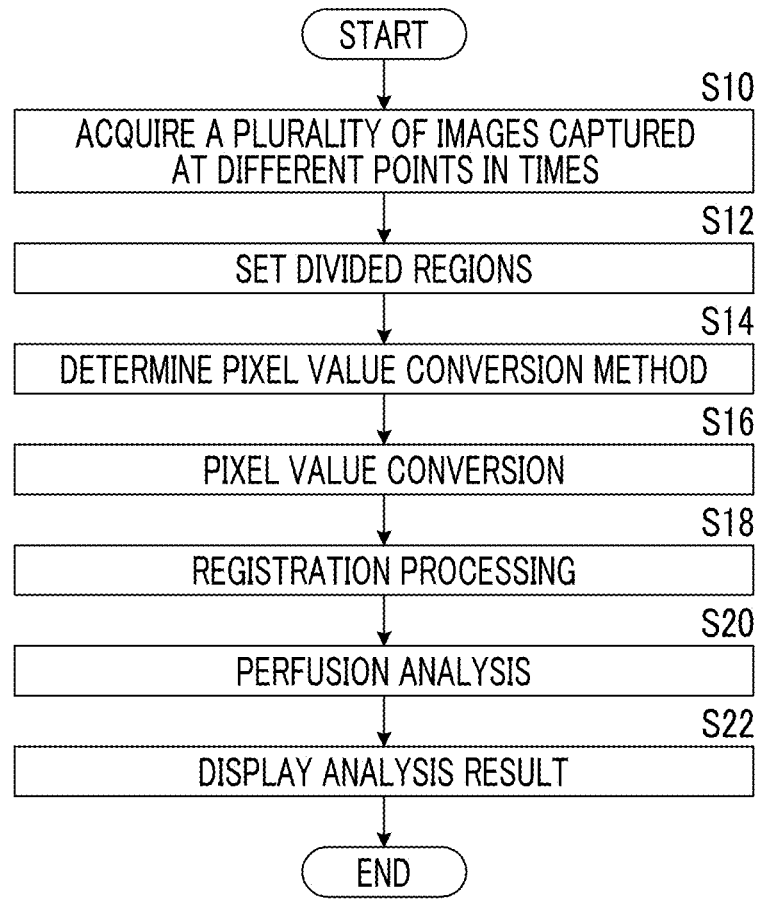
FIG. 4 is a flowchart illustrating the operation of the medical image diagnosis assistance system using the first embodiment of the image registration device of the invention.

Next, the operation of the medical image diagnosis assistance system of the present embodiment will be described with reference to the flowchart shown in FIG. 4.

First, based on the input of identification information of a patient from the user, two or more three-dimensional images 6 obtained by perfusion imaging of the patient's heart are acquired by the image acquisition unit 10 (S10).

The two or more three-dimensional images 6 acquired by the image acquisition unit 10 are input to the divided region setting unit 11. The divided region setting unit 11 sets a first divided region and a second divided region for each of the two or more three-dimensional images 6 (S12).

Then, the pixel value conversion method determination unit 12 determines a pixel value conversion method for the first divided region based on the average pixel value of the first divided region of each three-dimensional image 6, and determines a pixel value conversion method for the second divided region based on the average pixel value of each second divided region of three-dimensional images 6 (S14).

Then, using the pixel value conversion method determined by the pixel value conversion method determination unit 12, the pixel value conversion unit 13 performs pixel value conversion for the first and second divided regions of each three-dimensional image 6 (S16).

Then, the three-dimensional image 6 subjected to the pixel value conversion is input to the registration processing unit 14, and registration processing is performed by the registration processing unit 14 (S18).

The three-dimensional image 6 subjected to the registration processing is input to the perfusion analysis unit 15, and the perfusion analysis unit 15 performs perfusion analysis using the input three-dimensional image 6 (S20).

The perfusion analysis result of the perfusion analysis unit 15 is input to the display control unit 16, and the display control unit 16 displays the input perfusion analysis result on the display device 3 (S22).

According to the medical image diagnosis assistance system of the embodiment described above, a plurality of images including registration processing targets are acquired, and divided regions are set by dividing each registration processing target of the plurality of images. Then, for each set of divided regions set at the same position of the respective registration processing targets, a pixel value conversion method for each divided region is determined based on the pixel value of each divided region of the set. Pixel value conversion is performed on an image in each divided region of the set of divided regions using the determined pixel value conversion method for the divided region, and registration processing is performed on a plurality of images subjected to the pixel value conversion. By performing pixel value conversion using a pixel value conversion method that is determined for each divided region as described above, it is possible to reduce the contrast difference between images even in a case where a structure having a high pixel value in one image shows a low pixel value in the other image. As a result, it is possible to perform registration with high accuracy.

In the first embodiment described above, the divided region setting unit 11 sets, as divided regions, the first divided region including the right atrium and the right ventricle and the second divided region including the left atrium and the left ventricle. However, the divided region setting method is not limited thereto. For example, a first divided region including the right atrium and the right ventricle, a second divided region including the left atrium and the left ventricle, and a third divided region including the myocardium may be set as divided regions.

Alternatively, a first divided region including the right atrium, a second divided region including the right ventricle, a third divided region including the left atrium, and a fourth divided region including the left ventricle may be set as divided regions. Alternatively, a first divided region including the right atrium, a second divided region including the right ventricle, a third divided region including the left atrium, a fourth divided region including the left ventricle, and a fifth divided region including the myocardium may be set as divided regions.

Figure 5:
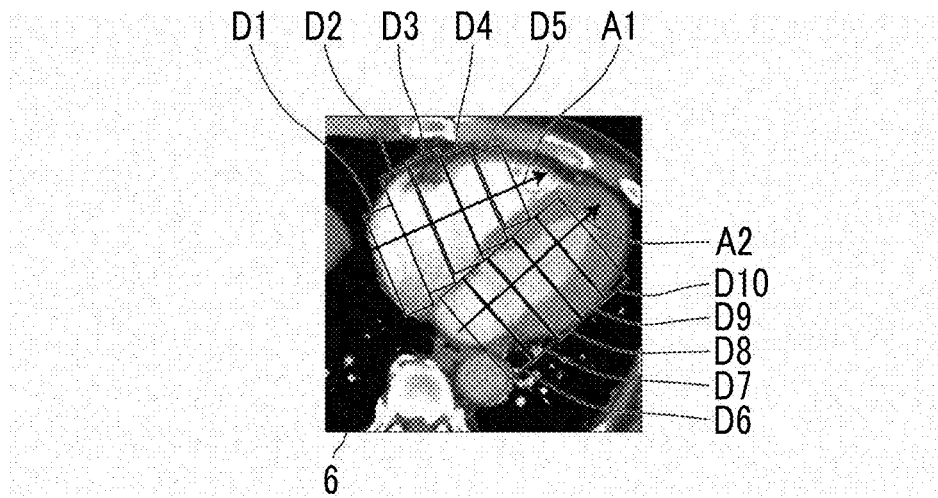
FIG. 5 is a diagram showing an example of divided regions set by dividing a cardiac image with a cross section perpendicular to the blood flow direction of the heart.

Instead of setting divided regions based on the anatomical structure of the heart as described above, divided regions may be set by dividing the heart with a cross section perpendicular to the blood flow direction of the heart in consideration of the direction in which the contrast medium changing the pixel value flows. FIG. 5 is a diagram showing an example in which divided regions are set by dividing the heart with a cross section perpendicular to the blood flow direction of the heart. Arrow A1 shown in FIG. 5 indicates the blood flow direction in the right atrium and the right ventricle, and arrow A2 indicates the blood flow direction in the left atrium and the left ventricle, and D1 to D10 indicate divided regions set by dividing the heart with cross sections perpendicular to the blood flow direction of the heart. Hereinafter, a method of determining a pixel value conversion method for each divided region in a case where the divided regions D1 to D10 are set as shown in FIG. 5 will be described.

First, the pixel value conversion method determination unit 12 checks the average pixel value of each divided region along the blood flow direction for both the first three-dimensional image 6 and the second three-dimensional image 6. Specifically, in the case of the example shown in FIG. 5, the average pixel value of each divided region is checked along the arrow A1, and the average pixel value of each divided region is checked along the arrow A2. Then, a divided region whose average pixel value is equal to or greater than a threshold value set in advance. That is, a divided region where the pixel value is increased by the contrast medium is specified.

Then, for divided regions at the same position between the first three-dimensional image 6 and the second three-dimensional image 6, in a case where the average pixel value of only one of the divided regions is equal to or greater than a threshold value, the pixel value conversion method determination unit 12 determines the divided region as a divided region to be subjected to pixel value conversion. Conversely, for divided regions at the same position between the first three-dimensional image 6 and the second three-dimensional image 6, in a case where the average pixel values of both the divided regions are equal to or greater than a threshold value or less than the threshold value, the pixel value conversion method determination unit 12 determines the divided region as a divided region that is not to be subjected to pixel value conversion.

Figure 6:
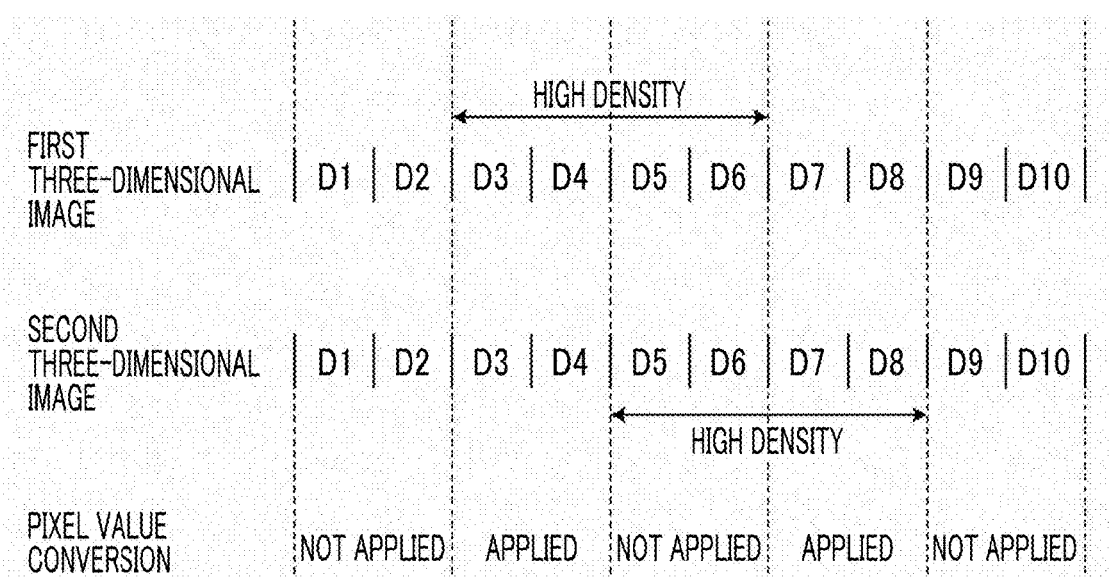
FIG. 6 is a diagram illustrating a method of determining a pixel value conversion method based on the pixel value of each divided region shown in FIG. 5.

FIG. 6 is a diagram illustrating the above method of determining a pixel value conversion method. As shown in FIG. 6, for example, in a case where the average pixel value of the divided regions D3 to D6 among the divided regions D1 to D10 of the first three-dimensional image 6 is equal to or greater than a threshold value and the average pixel value of the divided regions D5 to D8 among the divided regions D1 to D10 of the second three-dimensional image 6 is equal to or greater than the threshold value, the divided regions D3, D4, D7, and D8 are determined as divided regions to be subjected to pixel value conversion. On the other hand, the divided regions D1, D2, D5, D6, D9, and D10 are determined as divided regions that are not to be subjected to pixel value conversion.

Pixel value conversion and registration processing after determining the pixel value conversion method are the same as those in the first embodiment described above.

Figure 7:
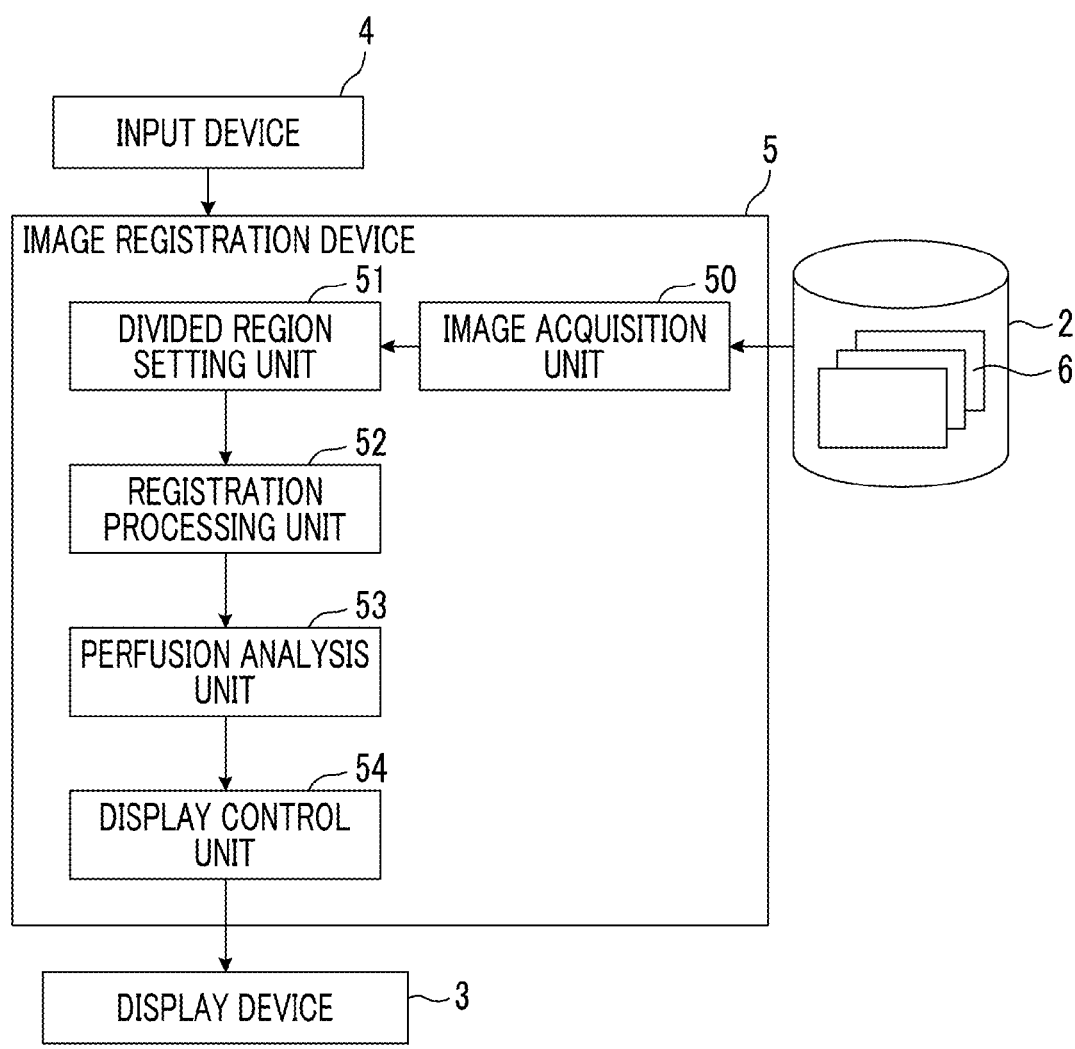
FIG. 7 is a block diagram showing the schematic configuration of a medical image diagnosis assistance system using a second embodiment of an image registration device of the invention.

Next, a medical image diagnosis assistance system using a second embodiment of the invention will be described. FIG. 7 is a block diagram showing the schematic configuration of a medical image diagnosis assistance system of the second embodiment. The medical image diagnosis assistance system of the second embodiment is different from the medical image diagnosis assistance system of the first embodiment in terms of the configuration of the image registration device 5. Other configurations are the same as the configurations of the first embodiment.

The image registration device 5 of the second embodiment includes an image acquisition unit 50, a divided region setting unit 51, a registration processing unit 52, a perfusion analysis unit 53, and a display control unit 54. Since the image acquisition unit 50, the divided region setting unit 51, the perfusion analysis unit 53, and the display control unit 54 are the same as the image acquisition unit 10, the divided region setting unit 11, the perfusion analysis unit 15, and the display control unit 16 of the first embodiment, the explanation thereof will be omitted.

For each set of divided regions set at the same position of the first three-dimensional image 6 and the second three-dimensional image 6, the registration processing unit 52 of the second embodiment performs registration processing by evaluating the degree of matching between the respective divided regions of the set using an evaluation function.

The registration processing of the second embodiment is the same as the registration processing of the first embodiment in that the registration processing unit 52 performs registration processing by evaluating the degree of matching between the respective divided regions using an evaluation function, but is different from the registration processing of the first embodiment in that, for each set of divided regions, the registration processing unit 52 performs registration processing by changing the evaluation function based on the pixel value of each divided region of the set.

Specifically, the registration processing unit 52 calculates an average pixel value of the first divided region of the first three-dimensional image 6 and an average pixel value of the first divided region of the second three-dimensional image 6. Then, in a case where the average pixel value of the first divided region of the first three-dimensional image 6 is 100 or more and the average pixel value of the first divided region of the second three-dimensional image 6 is less than 100, that is, in a case where the contrast of the first divided region of the first three-dimensional image 6 is different from the contrast of the first divided region of the second three-dimensional image 6, the degree of matching is calculated using an evaluation function of the following Equation (3) and registration processing is performed.

$$S_1(I_F(\cdot), I_M(T(\cdot; \mu))) = \frac{1}{N} \sum_{i=1}^{N} \min\{ \{I_F(x_i) - I_M(T(x_i; \mu))\}^2, \{f(I_F(x_i)) - I_M(T(x_i; \mu))\}^2 \} \quad (3)$$

$S_1$ in the above Equation (3) is an evaluation function of the degree of matching. In a case where the pixel values of corresponding divided regions between images are different, the value of $S_1$ decreases as the degree of matching between the positions of divided regions of the respective images increases. In addition, N is the total number of pixels to be compared between images (between a Fixed image and a Moving image), f is the pixel value conversion function of the above Equation (2), $x_i$ is a coordinate point, $I_F(x_i)$ is a pixel value at $x_i$ of the Fixed image, $I_M(x_i)$ is a pixel value at $x_i$ of the Moving image, T is a geometric transformation function of the coordinate point, and $\mu$ is a parameter of geometric transformation. It is assumed that one of the first three-dimensional image 6 and the second three-dimensional image 6 is the Fixed image and the other one is the Moving image.

Conversely, also in a case where the average pixel value of the first divided region of the first three-dimensional image 6 is less than 100 and the average pixel value of the first divided region of the second three-dimensional image 6 is 100 or more, the degree of matching is calculated using the evaluation function of the above Equation (3), and registration processing is performed.

On the other hand, in a case where both the average pixel value of the first divided region of the first three-dimensional image 6 and the average pixel value of the first divided region of the second three-dimensional image 6 are 100 or more or less than 100, that is, in a case where both the contrast of the first divided region of the first three-dimensional image 6 and the contrast of the first divided region of the second three-dimensional image 6 are close to each other, the degree of matching is calculated using an evaluation function of the following Equation (4) and registration processing is performed. Also in a case where both the average pixel value of the second divided region of the first three-dimensional image 6 and the average pixel value of the second divided region of the second three-dimensional image 6 are 100 or more or less than 100, the degree of matching is calculated using an evaluation function of the following Equation (4) and registration processing is performed in the same manner as for the first divided region.

$$S_2(I_F(\cdot), I_M(T(\cdot; \mu))) = \frac{1}{N} \sum_{i=1}^{N} \{I_F(x_i) - I_M(T(x_i; \mu))\}^2 \quad (4)$$

$S_2$ in the above Equation (4) is an evaluation function of the degree of matching, and the value of $S_2$ decreases as the degree of matching between pixel values increases. In addition, N is the total number of pixels to be compared between images (between a Fixed image and a Moving image), f is the pixel value conversion function of the above Equation (2), $x_i$ is a coordinate point, $I_F(x_i)$ is a pixel value at $x_i$ of the Fixed image, $I_M(x_i)$ is a pixel value at $x_i$ of the Moving image, T is a geometric transformation function of the coordinate point, and $\mu$ is a parameter of geometric transformation.

For the registration processing itself, for example, the method described in "Survey of medical image registration", Mani, VRS and others, Journal of Biomedical Engineering and Technology (2013), Vol. 1, No. 2, pp. 8-25 can be used.

Figure 8:
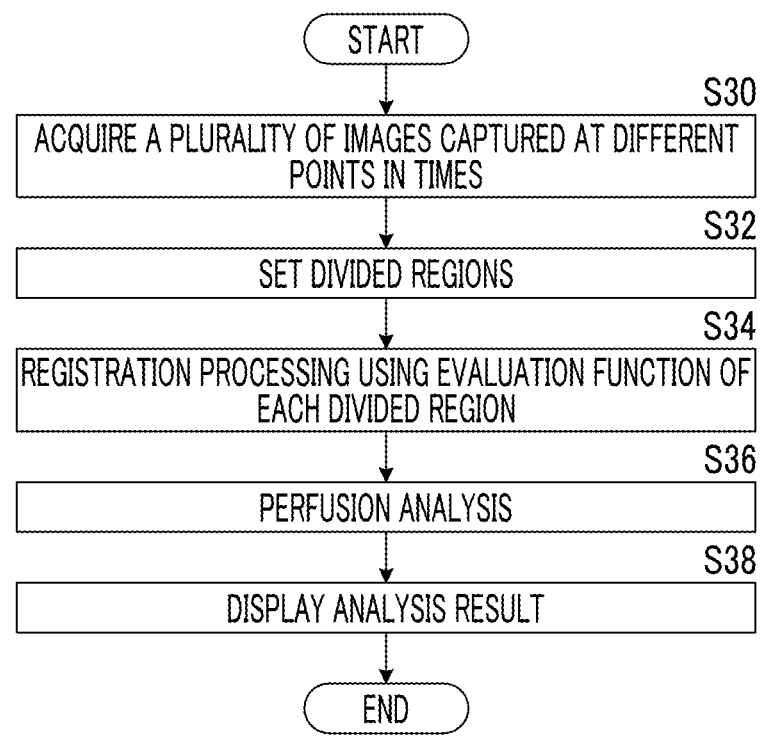
FIG. 8 is a flowchart illustrating the operation of the medical image diagnosis assistance system using the second embodiment of the image registration device of the invention.

Next, the operation of a medical image diagnosis assistance system of a second embodiment will be described with reference to the flowchart shown in FIG. 8.

First, based on the input of identification information of a patient from the user, two or more three-dimensional images 6 obtained by perfusion imaging of the patient's heart are acquired by the image acquisition unit 50 (S30).

The two or more three-dimensional images 6 acquired by the image acquisition unit 50 are input to the divided region setting unit 51. The divided region setting unit 51 sets a first divided region and a second divided region for each of the two or more three-dimensional images 6 (S32).

Then, the registration processing unit 52 determines an evaluation function for the first divided region based on the average pixel value of the first divided region of each three-dimensional image 6, determines an evaluation function for the second divided region based on the average pixel value of the second divided region of each three-dimensional image 6, and calculates the degree of matching using the evaluation functions determined for the first and second divided regions, thereby performing registration processing on each three-dimensional image 6 (S34).

The three-dimensional image 6 subjected to the registration processing is input to the perfusion analysis unit 53, and the perfusion analysis unit 53 performs perfusion analysis using the input three-dimensional image 6 (S36).

The perfusion analysis result of the perfusion analysis unit 53 is input to the display control unit 54, and the display control unit 54 displays the input perfusion analysis result on the display device 3 (S38).

According to the medical image diagnosis assistance system of the second embodiment described above, a plurality of images including registration processing targets are acquired, and divided regions are set by dividing each registration processing target of the plurality of images. Then, for each set of divided regions set at the same position of the respective registration processing targets, registration processing is performed by evaluating the degree of matching between the respective divided regions of the set using an evaluation function. At this time, for each set of divided regions, by changing the evaluation function based on the pixel value of each divided region of the set, the registration processing is performed. By performing registration processing by changing the evaluation function for each divided region as described above, it is possible to reduce the contrast difference between images even in a case where a structure having a high pixel value in one image shows a low pixel value in the other image. As a result, it is possible to perform registration with high accuracy.

In the second embodiment described above, the evaluation functions of the above Equations (3) and (4) are switched and used based on the pixel value of each divided region. However, evaluation functions are not limited thereto, and the following Equation (5) may be used instead of the above Equation (3).

$$S(I_F(\cdot), I_M(T(\cdot;\mu))) = \tag{5}$$
$$-\frac{1}{N}\sum_{i=1}^{N} k \cdot \exp\left\{-\frac{(I_F(x_i) - I_M(T(x_i;\mu)))^2}{2\sigma^2}\right\}\{I_F(x_i) - I_M(T(x_i;\mu))\}^2$$

S in the above Equation (5) is an evaluation function of the degree of matching, and the value of S decrease as the degree of matching between pixel values increases. In addition, N is the total number of pixels to be compared between images (between a Fixed image and a Moving image), $x_i$ is a coordinate point, $I_F(x_i)$ is a pixel value at $x_i$ of the Fixed image, $I_M(x_i)$ is a pixel value at $x_i$ of the Moving image, T is a geometric transformation function of the coordinate point, $\mu$ is a parameter of geometric transformation, and k and $\sigma$ are constants.

Similar to the above Equation (3), S in the above Equation (5) is an evaluation function of the degree of matching. In a case where the pixel values of corresponding divided regions between images are different, the value of S decreases as the degree of matching between the positions of divided regions of the respective images increases. In addition, N is the total number of pixels to be compared between images (between a Fixed image and a Moving image), $x_i$ is a coordinate point, $I_F(x_i)$ is a pixel value at $x_i$ of the Fixed image, $I_M(x_i)$ is a pixel value at $x_i$ of the Moving image, T is a geometric transformation function of the coordinate point, $\mu$ is a parameter of geometric transformation, and k and $\sigma$ are constants. S in the above Equation (5) is a function that decreases as the difference in pixel value approaches a predetermined value determined by the constant $\sigma$ so that the degree of matching increases.

In the first to third embodiments described above, the divided region setting unit 11 sets divided regions using the atlas image of the heart. However, the divided region setting method is not limited thereto. Hereinafter, a method of setting other divided regions will be described.

First, since the aorta is connected to the left ventricle, a change in pixel value due to the contrast medium is close to that in the left atrium and the left ventricle. Using this, an image of the phase in which the pixel values of the left atrium and the left ventricle are increased by the contrast medium is specified.

Specifically, first, regions of the aorta are extracted from the three-dimensional image 6 of two or more phases. As described above, regions of V shown in FIGS. 2A to 2C are the regions of the aorta. As a method of extracting the region of the aorta, known image processing can be used.

Then, based on a change in the average pixel value of the region of the aorta of each three-dimensional image 6, a three-dimensional image of the phase in which the pixel values of the left atrium and the left ventricle are higher than the pixel values of the right atrium and the right ventricle is specified. Specifically, based on the change in the average pixel value of the region of the aorta of each three-dimensional image, the three-dimensional image 6 of the phase in which the average pixel value of the region of the aorta is maximized is specified. Then, regions of the left atrium and the left ventricle are extracted by specifying regions, in which the pixel values are equal to or greater than a threshold value set in advance, in the specified three-dimensional image 6.

Then, among three-dimensional images in which the average pixel value of the region of the aorta is equal to or greater than a lower limit set in advance, a three-dimensional image of the phase in which the average pixel value of the region of the aorta is the smallest is specified as a three-dimensional image of the phase in which the pixel values of the right atrium and the right ventricle are higher than the pixel values of the left atrium and the left ventricle. Then, regions of the right atrium and the right ventricle are extracted by specifying regions, in which the pixel values are equal to or greater than a threshold value set in advance, in the specified three-dimensional image 6.

Then, the regions of the right atrium and the right ventricle extracted as described above are set as the first divided region, and the regions of the left atrium and the right ventricle extracted as described above are set as the second divided region.

The method of setting the first and second divided regions is not limited to the above-described method. For example, regions of the right atrium and the right ventricle and regions of the left atrium and the left ventricle may be extracted from the three-dimensional image 6 by using an image processing method, such as known contour extraction, and the first and second divided regions may be set using the extraction result.

EXPLANATION OF REFERENCES 1, 5: image registration device
2: medical image storage server
3: display device
4: input device
6: three-dimensional image
10: image acquisition unit
11: divided region setting unit
12: pixel value conversion method determination unit
13: pixel value conversion unit
14: registration processing unit
15: perfusion analysis unit
16: display control unit
50: image acquisition unit
51: divided region setting unit
52: registration processing unit
53: perfusion analysis unit
4: display control unit
A1: arrow showing blood flow direction in right atrium and right ventricle
A2: arrow showing blood flow direction in left atrium and left ventricle
D1 to D10: divided region
IR: region of interest
K: constant
L1: region of left atrium
L2: region of left ventricle
M: region of myocardium
R1: region of right atrium
R2: region of right ventricle
V: region of aorta

What is claimed is:

1. An image registration device, comprising:
a processor configured to:
acquire a plurality of images, each of the plurality of images including a registration processing target;
for each of the plurality of images, divide the registration processing target into a plurality of divided regions including a first divided region having a right atrium and a right ventricle and a second divided region having a left atrium and a left ventricle;
determine a plurality of sets of divided regions, each of the plurality of sets of divided regions comprising one of the plurality of divided regions of one image of the plurality of images and one of the plurality of divided regions of another image of the plurality of images located at a location corresponding to the one of the divided regions of the one image of the plurality of images;
for each of the plurality of sets of divided regions, determine a contrast difference between values of pixels in the one of the divided regions of the one image of the plurality of images and values of pixels in the one of the divided regions of the another image of the plurality of images;
determine a pixel value conversion method for each of the plurality of sets of divided regions where the contrast difference is greater than a threshold, the pixel value conversion method reducing the contrast difference;
for each of the plurality of sets of divided regions where the contrast difference is greater than the threshold, perform pixel value conversion of at least one of the values of pixels in the one of the divided regions of the one image of the plurality of images and the values of pixels in the one of the divided regions of the another image of the plurality of images; and
perform registration processing on the plurality of images based on the pixel value conversion,
wherein the right atrium, the right ventricle, the left atrium, and left ventricle are regions of a heart.

2. The image registration device according to claim 1, wherein the processor sets the first and second divided regions based on a change in pixel values of the registration processing target.

3. The image registration device according to claim 2, wherein the processor specifies a first image, in which pixel values of regions of the right atrium and the right ventricle are higher than pixel values of regions of the left atrium and the left ventricle, and a second image, in which the pixel values of the regions of the left atrium and the left ventricle are higher than the pixel values of the regions of the right atrium and the right ventricle, among the plurality of images based on the change in pixel values of the registration processing target, and sets the first divided region using the first image and sets the second divided region using the second image.

4. The image registration device according to claim 1, wherein the processor further sets, as the divided regions, a third divided region including a myocardium.

5. The image registration device according to claim 1, wherein the processor further sets, as the divided regions, a third divided region including a left atrium, a fourth divided region including a left ventricle, a fifth divided region including a right atrium, and a sixth divided region including a right ventricle.

6. The image registration device according to claim 5, wherein the processor further sets, as the divided regions, a seventh divided region including a myocardium.

7. The image registration device according to claim 1, wherein the processor sets a plurality of divided regions by dividing the registration processing target with a cross section perpendicular to a blood flow direction of the heart.

8. The image registration device according to claim 1, wherein the processor sets the divided regions using a standard image in which regions corresponding to the divided regions are set in advance.

9. The image registration device according to claim 1, wherein the plurality of images are captured at different points in time.

10. The image registration device according to claim 1, wherein the plurality of images are captured at a timing of a same cardiac phase in a plurality of heart beats.

11. An image registration device, comprising:
a processor configured to:
acquire a plurality of images, each of the plurality of images including a registration processing target;
for each of the plurality of images, divide the registration processing target into a plurality of divided regions including a first divided region having a right atrium and a right ventricle and a second divided region having a left atrium and a left ventricle;
determine a plurality of sets of divided regions, each of the plurality of sets of divided regions comprising one of the plurality of divided regions of one image of the plurality of images and one of the plurality of divided regions of another image of the plurality of images located at a location corresponding to the one of the divided regions of the one image of the plurality of images;

for each of the plurality of sets of divided regions, determine a contrast difference between values of pixels in the one of the divided regions of the one image of the plurality of images and values of pixels in the one of the divided regions of the another image of the plurality of images; and perform registration processing on the plurality of images based on an evaluation function, the evaluation function evaluating a degree of matching between the values of pixels in the one of the divided regions of the one image of the plurality of images and the values of pixels in the one of the divided regions of the another image of the plurality of images, wherein the processor determines the evaluation function based on at least one of the values of pixels in the one of the divided regions of the one image of the plurality of images and the values of pixels in the one of the divided regions of the another image of the plurality of images, wherein, for each of the plurality of sets of divided regions where the contrast difference is greater than a threshold, the evaluation function reduces the contrast difference and calculates the degree of matching, and wherein the right atrium, the right ventricle, the left atrium, and left ventricle are regions of a heart.

12. The image registration device according to claim 11, wherein the processor sets the first and second divided regions based on a change in pixel values of the registration processing target.

13. The image registration device according to claim 12, wherein the processor specifies a first image, in which pixel values of regions of the right atrium and the right ventricle are higher than pixel values of regions of the left atrium and the left ventricle, and a second image, in which the pixel values of the regions of the left atrium and the left ventricle are higher than the pixel values of the regions of the right atrium and the right ventricle, among the plurality of images based on the change in pixel values of the registration processing target, and sets the first divided region using the first image and sets the second divided region using the second image.

14. The image registration device according to claim 11, wherein the processor further sets, as the divided regions, a third divided region including a myocardium.

15. The image registration device according to claim 11, wherein the processor further sets, as the divided regions, a third divided region including a left atrium, a fourth divided region including a left ventricle, a fifth divided region including a right atrium, and a sixth divided region including a right ventricle.

16. The image registration device according to claim 15, wherein the processor further sets, as the divided regions, a seventh divided region including a myocardium.

17. The image registration device according to claim 11, wherein the processor sets a plurality of divided regions by dividing the registration processing target with a cross section perpendicular to a blood flow direction of the heart.

18. The image registration device according to claim 11, wherein the processor sets the divided regions using a standard image in which regions corresponding to the divided regions are set in advance.

19. The image registration device according to claim 11, wherein the plurality of images are captured at different points in time.

20. The image registration device according to claim 11, wherein the plurality of images are captured at a timing of a same cardiac phase in a plurality of heart beats.

21. An image registration method, comprising:
acquiring a plurality of images, each of the plurality of images including a registration processing target;

for each of the plurality of images, dividing the registration processing target into a plurality of divided regions including a first divided region having a right atrium and a right ventricle and a second divided region having a left atrium and a left ventricle;

determining a plurality of sets of divided regions, each of the plurality of sets of divided regions comprising one of the plurality of divided regions of one image of the plurality of images and one of the plurality of divided regions of another image of the plurality of images located at a location corresponding to the one of the divided regions of the one image of the plurality of images;

for each of the plurality of sets of divided regions, determining a contrast difference between values of pixels in the one of the divided regions of the one image of the plurality of images and values of pixels in the one of the divided regions of the another image of the plurality of images;

determining a pixel value conversion method for each of the plurality of sets of divided regions where the contrast difference is greater than a threshold, the pixel value conversion method reducing the contrast difference;

for each of the plurality of sets of divided regions where the contrast difference is greater than a threshold, performing pixel value conversion of at least one of the values of pixels in the one of the divided regions of the one image of the plurality of images and the values of pixels in the one of the divided regions of the another image of the plurality of images; and performing registration processing on the plurality of images based on the pixel value conversion, wherein the right atrium, the right ventricle, the left atrium, and left ventricle are regions of a heart.

22. A non-transitory computer-readable recording medium having stored therein an image registration program that causes a computer to:

acquire a plurality of images, each of the plurality of images including registration processing targets;

for each of the plurality of images, divide the registration processing target into a plurality of divided regions including a first divided region having a right atrium and a right ventricle and a second divided region having a left atrium and a left ventricle;

determine a plurality of sets of divided regions, each of the plurality of sets of divided regions comprising one of the plurality of divided regions of one image of the plurality of images and one of the plurality of divided regions of another image of the plurality of images located at a location corresponding to the one of the divided regions of the one image of the plurality of images;

for each of the plurality of sets of divided regions, determine a contrast difference between values of pixels in the one of the divided regions of the one image of the plurality of images and values of pixels in the one of the divided regions of the another image of the plurality of images; determine a pixel value conversion method for each of the plurality of sets of divided regions where the contrast difference is greater than a threshold, the pixel value conversion method reducing the contrast difference;

for each of the plurality of sets of divided regions where the contrast difference is greater than a threshold, perform pixel value conversion of at least one of the values of pixels in the one of the divided regions of the one image of the plurality of images and the values of pixels in the one of the divided regions of the another image of the plurality of images; and perform registration processing on the plurality of images based on pixel value conversion wherein the right atrium, the right ventricle, the left atrium, and left ventricle are regions of a heart.

23. An image registration device, comprising:
a memory in which commands to be executed by a computer are stored; and
a processor configured to execute the stored commands;
the processor executing the processes of:
acquiring a plurality of images, each of the plurality of images including a registration processing target;
for each of the plurality of images, dividing the registration processing target into a plurality of divided regions including a first divided region having a right atrium and a right ventricle and a second divided region having a left atrium and a left ventricle;
determining a plurality of sets of divided regions, each of the plurality of sets of divided regions comprising one of the plurality of divided regions of one image of the plurality of images and one of the plurality of divided regions of another image of the plurality of images located at a location corresponding to the one of the divided regions of the one image of the plurality of images;
for each of the plurality of sets of divided regions, determine a contrast difference between values of pixels in the one of the divided regions of the one image of the plurality of images and values of pixels in the one of the divided regions of the another image of the plurality of images; determining a pixel value conversion method for each of the plurality of sets of divided regions where the contrast difference is greater than a threshold, the pixel value conversion method reducing the contrast difference;
for each of the plurality of sets of divided regions where the contrast difference is greater than the threshold, performing pixel value conversion of at least one of the values of pixels in the one of the divided regions of the one image of the plurality of images and the values of pixels in the one of the divided regions of the another image of the plurality of images; and
performing registration processing on the plurality of images based on the pixel value conversion wherein the right atrium, the right ventricle, the left atrium, and left ventricle are regions of a heart.

24. An image registration method, comprising:
acquiring a plurality of images, each of the plurality of images including a registration processing target;
for each of the plurality of images, dividing the registration processing target into a plurality of divided regions including a first divided region having a right atrium and a right ventricle and a second divided region having a left atrium and a left ventricle;
determining a plurality of sets of divided regions, each of the plurality of sets of divided regions comprising one of the plurality of divided regions of one image of the plurality of images and one of the plurality of divided regions of another image of the plurality of images located at a location corresponding to the one of the divided regions of the one image of the plurality of images;
for each of the plurality of sets of divided regions, determining a contrast difference between values of pixels in the one of the divided regions of the one image of the plurality of images and values of pixels in the one of the divided regions of the another image of the plurality of images;
performing registration processing on the plurality of images based on an evaluation function, the evaluation function evaluating a degree of matching between the values of pixels in the one of the divided regions of the one image of the plurality of images and the values of pixels in the one of the divided regions of the another image of the plurality of images and determining the evaluation function based on at least one of the values of pixels in the one of the divided regions of the one image of the plurality of images and the values of pixels in the one of the divided regions of the another image of the plurality of images,
wherein, for each of the plurality of sets of divided regions where the contrast difference is greater than a threshold, the evaluation function reduces the contrast difference and calculates the degree of matching, and
wherein the right atrium, the right ventricle, the left atrium, and left ventricle are regions of a heart.

25. A non-transitory computer-readable recording medium having stored therein an image registration program that causes a computer to:
acquire a plurality of images, each of the plurality of images including a registration processing target;
for each of the plurality of images, divide the registration processing target into a plurality of divided regions including a first divided region having a right atrium and a right ventricle and a second divided region having a left atrium and a left ventricle;
determine a plurality of sets of divided regions, each of the plurality of sets of divided regions comprising one of the plurality of divided regions of one image of the plurality of images and one of the plurality of divided regions of another image of the plurality of images located at a location corresponding to the one of the divided regions of the one image of the plurality of images;
for each of the plurality of sets of divided regions, determine a contrast difference between values of pixels in the one of the divided regions of the one image of the plurality of images and values of pixels in the one of the divided regions of the another image of the plurality of images; and
perform registration processing on the plurality of images based on an evaluation function, the evaluation function evaluating a degree of matching between the values of pixels in the one of the divided regions of the one image of the plurality of images and the values of pixels in the one of the divided regions of the another image of the plurality of images,
wherein the processor determines the evaluation function based on at least one of the values of pixels in the one of the divided regions of the one image of the plurality of images and the values of pixels in the one of the divided regions of the another image of the plurality of images, wherein, for each of the plurality of sets of divided regions where the contrast difference is greater than a threshold, the evaluation function reduces the contrast difference and calculates the degree of matching, and wherein the right atrium, the right ventricle, the left atrium, and left ventricle are regions of a heart.

26. An image registration device, comprising:
a memory in which commands to be executed by a computer are stored; and
a processor configured to execute the stored commands;
the processor executing the processes of:
   acquiring a plurality of images, each of the plurality of images including a registration processing target;
   for each of the plurality of images, dividing the registration processing target into a plurality of divided regions including a first divided region having a right atrium and a right ventricle and a second divided region having a left atrium and a left ventricle;
   determining a plurality of sets of divided regions, each of the plurality of sets of divided regions comprising one of the plurality of divided regions of one image of the plurality of images and one of the plurality of divided regions of another image of the plurality of images located at a location corresponding to the one of the divided regions of the one image of the plurality of images;
   for each of the plurality of sets of divided regions, determining a contrast difference between values of pixels in the one of the divided regions of the one image of the plurality of images and values of pixels in the one of the divided regions of the another image of the plurality of images; and
   performing registration processing on the plurality of images based on an evaluation function, the evaluation function evaluating a degree of matching between the values of pixels in the one of the divided regions of the one image of the plurality of images and the values of pixels in the one of the divided regions of the another image of the plurality of images, wherein the processor determines the evaluation function based on at least one of the values of pixels in the one of the divided regions of the one image of the plurality of images and the values of pixels in the one of the divided regions of the another image of the plurality of images, wherein, for each of the plurality of sets of divided regions where the contrast difference is greater than a threshold value, the evaluation function reduces the contrast difference and calculates the degree of matching, and wherein a first divided region including a right atrium and a right ventricle and a second divided region including a left atrium and a left ventricle are set as the divided regions wherein the right atrium, the right ventricle, the left atrium, and left ventricle are regions of a heart.

* * * * *